(12) United States Patent
Fernandes (10) Patent No.: US 9,480,679 B2
(45) Date of Patent: Nov. 1, 2016

(54) METHODS FOR TREATING MALARIA, TUBERCULOSIS AND MAC DISEASES

(75) Inventor: Prabhavathi Fernandes, Chapel Hill, NC (US)

(73) Assignee: CEMPRA PHARMACEUTICALS, INC., Chapel Hill, NC (US)

( * ) Notice: Subject to any disclaimer, the term of this patent is extended or adjusted under 35 U.S.C. 154(b) by 0 days.

(21) Appl. No.: 13/395,255

(22) PCT Filed: Sep. 10, 2010

(86) PCT No.: PCT/US2010/048540
§ 371 (c)(1),
(2), (4) Date: Mar. 9, 2012

(87) PCT Pub. No.: WO2011/032052
PCT Pub. Date: Mar. 17, 2011

(65) Prior Publication Data
US 2012/0172323 A1   Jul. 5, 2012

Related U.S. Application Data (60) Provisional application No. 61/241,258, filed on Sep. 10, 2009.

(51) Int. Cl.
A61K 31/70 (2006.01)
A61K 31/4192 (2006.01)
A61K 31/7048 (2006.01)

(52) U.S. Cl.
CPC ....... *A61K 31/4192* (2013.01); *A61K 31/7048* (2013.01)

(58) Field of Classification Search
CPC .................................................. A61K 31/7048
USPC .......................................................... 514/29
See application file for complete search history.

(56) References Cited

U.S. PATENT DOCUMENTS

| | | |
|---|---|---|
| 1,354,753 A | 10/1920 | Howard |
| 2,180,006 A | 11/1939 | Hasche |
| 3,668,282 A | 6/1972 | Below |
| 3,843,787 A | 10/1974 | Fabrizio |
| 4,312,866 A | 1/1982 | Caruso |
| 4,331,803 A | 5/1982 | Watanabe |
| 4,474,768 A | 10/1984 | Bright |
| 4,742,049 A | 5/1988 | Baker |
| 4,886,792 A | 12/1989 | Djokic |
| 4,990,602 A | 2/1991 | Morimoto |
| 5,211,955 A | 5/1993 | Legros |
| 5,444,051 A | 8/1995 | Agouridas |
| 5,527,780 A | 6/1996 | Agouridas |
| 5,543,400 A | 8/1996 | Agouridas |
| 5,635,485 A | 6/1997 | Agouridas |
| 5,656,607 A | 8/1997 | Agouridas |
| 5,747,467 A | 5/1998 | Agouridas |
| 5,760,233 A | 6/1998 | Agouridas |
| 5,770,579 A | 6/1998 | Agouridas |
| 5,834,428 A | 11/1998 | Drucker |
| 5,985,844 A | 11/1999 | Heck |
| 6,011,142 A | 1/2000 | Bonnet |
| 6,020,521 A | 2/2000 | Randolph |
| 6,028,181 A | 2/2000 | Or |
| 6,096,714 A | 8/2000 | Agouridas |
| 6,096,922 A | 8/2000 | Lal |
| 6,121,432 A | 9/2000 | Bonnet |
| 6,270,768 B1 | 8/2001 | OConnell |
| 6,313,101 B1 | 11/2001 | Denis |
| 6,395,300 B1 | 5/2002 | Straub et al. |
| 6,395,710 B1 | 5/2002 | Chu |
| 6,407,074 B1 | 6/2002 | Bronk |
| 6,407,257 B1 | 6/2002 | Agouridas et al. |
| 6,420,535 B1 | 7/2002 | Phan |
| 6,437,106 B1 | 8/2002 | Stoner |
| 6,440,941 B1 | 8/2002 | Denis |
| 6,455,505 B2 | 9/2002 | Agouridas |
| 6,515,116 B2 | 2/2003 | Suh |
| 6,555,524 B2 | 4/2003 | Kaneko |
| 6,664,238 B1 | 12/2003 | Su |
| 6,777,393 B2 | 8/2004 | Bronk |
| 6,809,188 B1 | 10/2004 | Suh |
| 6,849,608 B2 | 2/2005 | Su |
| 6,890,907 B2 | 5/2005 | Speirs |
| 7,163,924 B2 | 1/2007 | Burger |
| 7,332,476 B2 | 2/2008 | Burger |
| 7,375,234 B2 | 5/2008 | Sharpless |

(Continued)

FOREIGN PATENT DOCUMENTS

| | | |
|---|---|---|
| CN | 1354753 | 6/2002 |
| CN | 101045063 | 10/2007 |

(Continued)

OTHER PUBLICATIONS

Barthel et al, "Telithromycin and Quinuprisin-Dalfopristin Induce Delayed Death in Plasmodium falciparum", Antimicrobial Agents and Chemotherapy, Feb. 2008, vol. 52, No. 2, pp. 774-777.*

Sumerkan, B., Aygen, B., Doganay, M., & Sehmen, E. (1996). Antimicrobial susceptibility of Bacillus anthracis against macrolides. Salisbury Med Bull Supplement, 87, 138.

Rostovtsev, V.V. et al., 'A Stepwise Huisgen Cycloaddition Process: Copper(I)=Catalyzed Regioselective 'Ligation' of Azides and Terminal Alkynes,' Angew. Chem. Int. Ed., 41: 2596-2599 (2002).

Torne et al. 'Peptidotriazoles on Solid Phase: [1,2,3]-Triazoles by Regiospecific Copper(I)Catalyzed 1,3-Dipolar Cycloadditions of Terminal Alkynes to Azides', J. Org. Chem., 67:3057-64 (2002).

Vennerstrom, Jonathan L., et al., "Identification of an Antimalarial Synthetic Trioxolane Drug Development Candidate", 2004, Letters to Nature, vol. 430, pp. 900-904.

(Continued)

*Primary Examiner* — Leigh C Maier
(74) *Attorney, Agent, or Firm* — Brannon Sowers & Cracraft PC (57) ABSTRACT

Described herein are formulations and methods for treating diseases caused by infectious pathogens, including *mycobacterium avium* complex, *mycobacterium tuberculosis*, Nocardia, *Plasmodium falcium*, and *Plasmodium berghei*.

17 Claims, 2 Drawing Sheets

(56) References Cited

U.S. PATENT DOCUMENTS

| | | |
|---|---|---|
| 7,419,961 B2 | 9/2008 | Napoletano |
| 7,601,695 B2 | 10/2009 | Liang |
| 8,247,394 B2 | 8/2012 | Fernandes |
| 8,791,080 B2 | 7/2014 | Fernandes |
| 8,796,232 B2 | 8/2014 | Fernandes |
| 9,051,346 B2 | 6/2015 | Pereira |
| 2002/0028781 A1 | 3/2002 | Agouridas |
| 2002/0044967 A1 | 4/2002 | Yamashita |
| 2003/0143162 A1 | 7/2003 | Speirs |
| 2003/0176327 A1 | 9/2003 | Cassell |
| 2004/0009930 A1 | 1/2004 | Su |
| 2004/0014685 A1 | 1/2004 | Mercep |
| 2005/0009764 A1 | 1/2005 | Burger et al. |
| 2005/0014706 A1* | 1/2005 | Falzari et al. ............ 514/28 |
| 2005/0022242 A1 | 1/2005 | Rosetti |
| 2005/0153905 A1 | 7/2005 | Burger |
| 2005/0209172 A1 | 9/2005 | Woo |
| 2005/0222427 A1 | 10/2005 | Sharpless |
| 2006/0100164 A1 | 5/2006 | Liang |
| 2006/0264385 A1 | 11/2006 | Wang |
| 2007/0015719 A1 | 1/2007 | Jenkins |
| 2007/0167382 A1 | 7/2007 | Finkelstein |
| 2007/0197518 A1 | 8/2007 | Johnson |
| 2007/0281894 A1 | 12/2007 | Gant |
| 2008/0113926 A1* | 5/2008 | Ivezic et al. ............ 514/29 |
| 2008/0221048 A1 | 9/2008 | Woo |
| 2008/0227730 A1 | 9/2008 | Mutak |
| 2008/0241959 A1 | 10/2008 | Culic |
| 2008/0287376 A1 | 11/2008 | Das |
| 2009/0075916 A1 | 3/2009 | Upadhyay |
| 2009/0076253 A1 | 3/2009 | Kashimura |
| 2009/0087389 A1 | 4/2009 | Leonard |
| 2009/0156517 A1 | 6/2009 | Zhang |
| 2010/0216731 A1 | 8/2010 | Pereira |
| 2011/0195920 A1 | 8/2011 | Fernandes |
| 2012/0071429 A1 | 3/2012 | Duffield |
| 2012/0172323 A1 | 7/2012 | Fernandes |
| 2013/0011453 A1 | 1/2013 | Latta |
| 2013/0018008 A1 | 1/2013 | Pereira |
| 2013/0045937 A1 | 2/2013 | Pereira |
| 2013/0053362 A1 | 2/2013 | Castro |
| 2013/0156705 A1 | 6/2013 | Zhang |
| 2013/0164351 A1 | 6/2013 | Fernandes |
| 2013/0172280 A1 | 7/2013 | Pereira |
| 2013/0345410 A1 | 12/2013 | Liang |
| 2014/0088062 A1 | 3/2014 | Pereira |
| 2014/0148431 A1 | 5/2014 | Patel |

FOREIGN PATENT DOCUMENTS

| | | |
|---|---|---|
| EP | 0248279 A2 | 12/1987 |
| EP | 0680967 A1 | 11/1995 |
| EP | 1024145 A2 | 8/2000 |
| EP | 1167375 | 1/2002 |
| GB | 891817 | 3/1962 |
| JP | 06220082 | 8/1994 |
| JP | 08053489 | 2/1996 |
| JP | 2000507573 | 6/2000 |
| JP | 2000229993 | 8/2000 |
| JP | 2000351794 | 12/2000 |
| JP | 2002514197 | 5/2002 |
| JP | 2004502736 | 1/2004 |
| JP | 2006528667 | 12/2006 |
| JP | 2007536371 | 12/2007 |
| JP | 2008519788 | 6/2008 |
| JP | 2008534504 | 8/2008 |
| JP | 2009502788 | 1/2009 |
| RU | 2230748 | 6/2004 |
| WO | 9736912 | 10/1997 |
| WO | 9830574 A1 | 7/1998 |
| WO | 9856800 A1 | 12/1998 |
| WO | 9921866 A1 | 5/1999 |
| WO | 9928311 A1 | 6/1999 |
| WO | 0012521 A1 | 3/2000 |
| WO | 0031099 A1 | 6/2000 |
| WO | 0044761 A2 | 8/2000 |
| WO | 0062783 A2 | 10/2000 |
| WO | 0110878 | 2/2001 |
| WO | 0110878 A1 | 2/2001 |
| WO | 0250092 A1 | 6/2002 |
| WO | 03004509 | 1/2003 |
| WO | 03004509 A2 | 1/2003 |
| WO | 03072141 A1 | 9/2003 |
| WO | 2004080391 A2 | 9/2004 |
| WO | 2004101587 | 11/2004 |
| WO | 2005074945 | 8/2005 |
| WO | 2005105821 | 11/2005 |
| WO | 2005108412 | 11/2005 |
| WO | 2006050941 | 5/2006 |
| WO | 2006050942 | 5/2006 |
| WO | 2006087642 | 8/2006 |
| WO | 2007008537 | 1/2007 |
| WO | 2007059307 A2 | 5/2007 |
| WO | 2007060627 | 5/2007 |
| WO | 2007143507 | 12/2007 |
| WO | 2009055557 | 4/2009 |
| WO | 2009055557 A1 | 4/2009 |
| WO | 2010048599 | 4/2010 |
| WO | 2010048600 | 4/2010 |
| WO | 2010048601 | 4/2010 |
| WO | 2011008193 | 1/2011 |
| WO | 2011112864 A1 | 9/2011 |
| WO | 2011119604 | 9/2011 |
| WO | 2011146829 | 11/2011 |
| WO | 2012042534 | 4/2012 |
| WO | 2013148891 | 10/2013 |
| WO | 2014145210 | 9/2014 |
| WO | 2014152326 | 9/2014 |
| WO | 2014165792 | 10/2014 |
| WO | 2015181723 | 12/2015 |

OTHER PUBLICATIONS

Baker, William R., et al. "Modification of macrolide antibiotics. Synthesis of 11-deoxy-11-(carboxyamino)-6-O-methylerythromycin A 11, 12-(cyclic esters) via an intramolecular Michael reaction of O-carbamates with an. alpha.,. beta.-unsaturated ketone." The Journal of Organic Chemistry 53.10 (1988): 2340-2345.

Barcia-Macay, Maritza, et al., 'Pharmacodynamic Evaluation of the Intracellular Activities of Antibiotics Against Staphylococcus Aureus in a Model of THP-1 Macrophages', 2006, Antimicrobial Agents and Chemotherapy. vol. 50, No. 3, pp: 841-851.

Bebear, C.M., et al., In vitro activity of trovafloxacin compared to those of five antimicrobials against mycoplasmas including Mycoplasma hominis and Ureaplasma urealyticum fluoroquinolone-resistant isolates that have been genetically characterized, Antimicrob Agents Chemother 44:2557-2560 (2000).

Berge, Stephen M., et al., "Pharmaceutical Salts", 1977, Journal of Pharmaceutical Sciences, vol. 66, No. 1, pp. 1-19.

Bermudez, Luiz E., et al., "EDP-420, a Bicyclolide (Bridged Bicyclic Macrolide), Is Active Against Mcyobacterium Avium", 2007, Antimicrobal Agents and Chemotherapy, vol. 51, No. 5, pp. 1666-1670.

Bermudez, Luiz E., et al., "Telithromycin is Active Against Mycobacterium Avium in Mice Despite Lacking Significant Activity in Standard in Vitro and Macrophage Assays and Is Associated with Low Frequency of Resistance During Treatment", 2001, Antimicrobal Agents and Chemotherapy, vol. 45, No. 8, pp. 2210-2214.

Birkenmeyer, R. D., Kroll, S. J., Lewis, C., Stern, K. F., and Zurenko, G. E., 'Synthesis and Antibacterial Activity of Clindamycin Analogues: Pirlimycin, a Potent Antibacterial Agent', Journal of Medicinal Chemistry, vol. 27, No. 2, 1984, 216-223.

Caira MR, "Crystalline polymorphism of orgainic compounds," Design of Organic Solids, Topics in Current Chemistry, Springer Berlin Heidelberg, 1998, p. 163-208.

Celebuski, J.E. et al., 'Chemical Modification of Erythromycin: Novel Reaction Observed by Treatment with Metalloporphyrins', vol. 35, No. 23, pp. 3837-3850, 1994, Elsevier Science Ltd.

(56) References Cited

OTHER PUBLICATIONS

Champney et al., 'Structure-Activity Relationships for Six Ketolide Antibiotics', Current Microbiology, 42:203-10 (2001).
Crone, Julia, et al., "Evaluation of a monoclonal antibody-based test for detection of Helicobacter pylori-Specific Antigen in stool samples from mice," Jul. 2004, Clinical and Diagnostic Laboratory Immunology, vol. 11, No. 4, pp. 799, 800.
Cynamon, M. H., et al., "Activity of ABT-773 Against Mycobacterium Avium Complex in the Beige Mouse Model", 2000, Antimicrobal Agents and Chemotherapy, vol. 44, No. 10, pp. 2895-2896.
Denis et al., beta-Keto-Ester Chemistry and Ketolides. Snythesis and antibacterial Activity of 2-Halogeno, 2-Methyl and 2,3 Enol-Ether Ketolides, Bioorganic & Medicinal Chemistry Letters, 10:2019-22 (2000).
Djokic, S. et al., 'Erythromycin Series. Part 11. Ring Expansion of Erythromycin A Oxime by the Beckmann Rearrangement.' J. Chem. Soc Perkin Trans 1., 1881-1890 (1986).
Drusano, G. L., et al., "Is 60 Days of Ciprofloxacin Adminstration Necessary for Postexposure Prophylaxis for Bacillus Anthracis?", 2008, Antimicrobial Agents and Chemotherapy. vol. 52, No. 11, pp. 3973-3979.
Duffy, L., et al., Fluoroquinolone resistance in Ureaplasma parvum in the United States, J Clin Microbiol 44:1590-1591 (2006).
Feder, P. I., et al., 1991. Statistical Analysis of Dose-Response Experiments by Maximum Likelihood Analysis and Iteratively Reweighted Nonlinear Least Squares Regression Techniques, 1991, Drug Information Journal, vol. 28, pp. 323-334.
Hill, D.R. et al., 'Novel Macrolides via meso-Tetraarylmetalloporphyrin Assisted Oxidation', Tetrahedron Letters, vol. 37, No. 6, pp. 787-790, 1996, Elsevier Science Ltd.
Holzer, G., et al., "Ka1,2 and KB1,3 X-Ray Emission Lines of the 3d Transition Metals", Dec. 1997, Physical Review, vol. 56, No. 6, pp. 4554-4568.
Inglesby, Thomas V., et al., "Anthrax as a Biological Weapon, 2002", 2002, Journal of the American Medical Association, vol. 287, No. 17, pp. 2236-2252.
Jensen, J.S., et al., Azithromycin Treatment Failure in Mycoplasma genitaliumPositive Patients with Nongonococcal Urethritis Is Associated with Induced Macrolide Resistance, Clin Infect Dis 47:1546-53 (2008).
Jones et al.: 'MIC Quality Control Guidelines and Disk Diffusion Test Optimization for CEM-101, a Novel Fluoroketolide' Journal of Clinical Microbiology vol. 48, No. 4, 30 Dec. 2009, pp. 1470-1473.
Katz, Leonard, and Gary W. Ashley. "Translation and protein synthesis: macrolides." Chemical reviews 105.2 (2005): 499-528.
Laine, Loren, et al., "Prospective comparison of H&E, Giemsa and Genta stains for the diagnosis of Helicobacter pylori," 1997, Gastrointestinal Endoscopy, vol. 45, No. 6, pp. 463-67.
Lee, Adrian, et al., "A standard mouse model of Helicobacter pylori infection: introducing the Sydney Strain," 1997, Gastroenterology, vol. 112, pp. 1386-97.
LeMahieu, R. A., Carson, M., and Kierstead, R. W., 'Glycoside Cleavage Reactions on erythromycin A. Preparation of Erythronolide A,' Journal of Medicinal Chemistry, vol. 17, No. 9, 1974, 953-956.
Lemaire, Sandrine, et al., "Cellular Accumulation and Pharmacodynamic Evaluation of the Intracellular Activity of Cem-101, a Novel Fluoroketolide, Against Staphylococcus Aureus, Listeria Monocytogenes and Legionella Pneumophila in Human Thp-1 Macrophages", 2009, Antimicrobial Agents and Chemotherapy. vol. 53, No. 9, pp. 3734-3743.
Li, X., et al., Emerging macrolide resistance in Mycoplasma pneumoniae in children: detection and characterization of resistant isolates, Pediatr Infect Dis J, 28:693-696 (2009).
Liang C. H. et al., 'Synthesis and biological activity of new 5-0-sugar modified ketolide and 2-fluoro-ketolide antibiotics,' Bioorganic & Medicinal Chemistry Letters, Pergamon, Elsevier Science, GB, vol. 15, No. 5, Mar. 1, 2005, pp. 1307-1310.

Morimoto S. et al., 'Chemical Modification of Erythromycins VII. Molecular Rearrangement Observed During Chemical Modification Study of the Desosamine Unit of Erythromycins', Heterocycles, Elsevier Science Publishers, vol. 31, No. 2, Jan. 1, 1990, pp. 305-319.
Nilius et al.: 'Ketolides: the future of the macrolides?' Current Opinion in Pharmacology, [Online] vol. 2, 14 Jan. 2002, pp. 1-8 Retrieved from the Internet: <URL:http://www.sciencedirect.com/science/article/pii/S1471489202001984>.
Or et al., 'Design, Synthesis, and Antimicrobial Activity of 6-0-Substituted Ketolides Active Against Resistant Respiratory Tract Pathogens', J. Med. Chem., 43:1045-49 (2000).
Patel, Ramesh N., "Stereoselective Biocatalysis", 2000, Bristol-Myers Squibb Research Institute; pp. 775-797.
Pathak et al., "Enzymatic Protecting Group Techniques in Organic Synthesis," Stereosel, Biocatal., 2000; pp. 775-797.
Phan, L.T. et al., 'Synthesis of 2-Fluoro-6-O-propargy1-11,12-carbamate Ketolides. A Novel Class of Antibiotics,' Org. Ltrs., 2:2951-2954 (2000).
Physicians' Desk Reference, p. 2905, (2007).
Plata et al., "The synthesis of ketolide antibiotic ABT-773 (cethromycin)," Tetrahedron.
Romero et al., 'An efficient entry to new sugar modified ketolide antibiotics' Tetrahedron Letters, vol. 46, 2005, pp. 1483-1487.
Vince, R., Almquist, R. G., Ritter, C. L., and Daluge, S., Antimicrobial Agents and Chemotherapy, vol. 8, No. 4, 1975, 439-443.
Waites, K.B., et al., Mycoplasmas and ureaplasmas as neonatal pathogens, Clin Microbiol Rev 18:757-89 (2005).
Zhenkun Ma & Peter A. Nemoto "Discovery and Development of Ketolides as a New Generation of MacrolideAntimicrobial Agents" Curr Med Chem-Anti-Infective Agents 1:15-34 (2002).
Zuckerman, "Macrolides and ketolides: azithromycin, clarithromycin, telithromycin", Infectious Disease Clinics of North America, vol. 18, (2004), pp. 621-649.
Threlfall, Terence L. "Analysis of organic polymorphs. A review." Analyst 120.10 (1995): 2435-2460.
Petit, Samuel, and Gérard Coquerel. "The amorphous state." Polymorphism: In the Pharmaceutical Industry 10 (2006): 1.
Organic Compounds Crystal Manufacture Handbook—Principles and Knowhow, 2008, pp. 57 to 84.
Hancock, Bruno C., Sheri L. Shamblin, and George Zografi. "Molecular mobility of amorphous pharmaceutical solids below their glass transition temperatures." Pharmaceutical research 12.6 (1995): 799-806.
Ashizawa, Kazuhide, "Physico-Chemical Studies on the Molecular Details of Drug Crystals," Phar Tech Japan, 2002, vol. 18, No. 10, pp. 81-96.
European Search Report for EP 09 82 2827, dated Mar. 21, 2012.
International Search Report for PCT/US2009/061977, dated Dec. 23, 2009, (3 pages).
PCT International Search Report and Written Opinion for PCT/US2011/029424, mailed May 25, 2011.
PCT Search Report/Written Opinion prepared for PCT/US2010/048540, mailed Oct. 21, 2010.
PCT Search Report and Written Opinion for PCT/US2011/037330 completed Aug. 26, 2011.
PCT Search Report and Written Opinion prepared for PCT/US2009/061978 mailed Dec. 9, 2009.
International Search Report Written Opinion for PCT/US2008/080936 completed Dec. 8, 2008.
Maurin, M., Mersali, N. F., & Raoult, D. (2000). Bactericidal activities of antibiotics against intracellular Francisella tularensis. Antimicrobial agents and chemotherapy, 44(12), 3428-3431.
Luna, V. A., King, D. S., Gulledge, J., Cannons, A. C., Amuso, P. T., & Cattani, J. (2007). Susceptibility of Bacillus anthracis, Bacillus cereus, Bacillus mycoides, Bacillus pseudomycoides and Bacillus thuringiensis to 24 antimicrobials using Sensititre® automated microbroth dilution and Etest® agar gradient diffusion methods. Journal of antimicrobial chemotherapy, 60(3), 555-567.
Barthel, D., Schlitzer, M., & Pradel, G. (2008). Telithromycin and quinupristin-dalfopristin induce delayed death in Plasmodium falciparum. Antimicrobial agents and chemotherapy, 52(2), 774-777.

(56) References Cited

OTHER PUBLICATIONS

Still, J. G., et al. "Single Oral Dose Pharmacokinetics and Safety of CEM-101 in Healthy Subjects." 46th Annual Meeting. Idsa, 2008.
Lee, Joo Hyun, and Myung Gull Lee. "Dose-dependent pharmacokinetics of telithromycin after intravenous and oral administration to rats: contribution of intestinal first-pass effect to low bioavailability." J. Pharm. Pharm. Sci 10 (2007): 37-50.
Chen, M., Muri, E. M., Jacob, T. M., & Williamson, J. S. (2003). Synthesis and bioactivity of erythromycin derivatives. Medicinal chemistry research, 12(3), 111-129.
Kerdesky, F. A., Premchandran, R., Wayne, G. S., Chang, S. J., Pease, J. P., Bhagavatula, L., . . . & King, S. A. (2002). Synthesis of 2'-O-Benzoyl-3-keto-6-O-propargyl-11, 12-carbamoyl Erythromycin A. Organic process research & development, 6(6), 869-875.
Zhu, Z. J., Krasnykh, O., Pan, D., Petukhova, V., Yu, G., Liu, Y., . . . & Franzblau, S. G. (2008). Structure-activity relationships of macrolides against Mycobacterium tuberculosis. Tuberculosis, 88, S49-S63.
Putnam S. D. et al, Antimicrobial Characterization Of Solithromycin (Cem-101), A Novel Fluroroketolide: Activity Against Staphlococci and Enterococci. International Journal of Antimicrobial Agents, vol. 37, No. 1, 2011, pp. 39-45.
Written Opinion, Singapore Application No. 11201405895U; Intellectual Property Office of Singapore; Mar. 31, 2015, 6 pages.
Database WPI Week 200822 Thomson Scientific, London, GB; AN 2008-402982.
Zimmermann, Torsten, et al. "Comparative tolerability of intravenous azithromycin, clarithromycin and erythromycin in healthy volunteers." Clinical Drug Investigation 21.8 (2001): 527-536.
Luke, D. R., and G. Foulds. "Toleration of intravenous azithromycin." The Annals of pharmacotherapy 31.9 (1997): abstract only.
Cannon, John B., N. Adeyinka Williams, and Karen J. Papp. "Reduction of pain on intravenous infusion with bile salt formulations for a macrolide antibiotic." International journal of pharmaceutics 114.1 (1995): abstract only.
Lu, Yan, YanJiao Wang, and Xing Tang. "Formulation and thermal sterile stability of a less painful intravenous clarithromycin emulsion containing vitamin E." International journal of pharmaceutics 346.1 (2008): abstract only.
Llano-Sotelo, B., D. Klepacki, and A. S. Mankin. 2008. Binding and action of CEM-10, a new macrolide/ketolide in development for treating infections with macrolide-resistant and macrolide-susceptible bacteria. 48th Annu. Intersci. Conf. Antimicrob. Agents Chemother./46th Infect. Dis. Soc. Am. Ann. Meet., abstr. F1-3983.
International Search Report for PCT/US2015/015353, dated May 14, 2015, (8 pages).
Ferris, C. F., Lu, S. F., Messenger, T., Guillon, C. D., Heindel, N., Miller, M., . . . & Simon, N. G. (2006). Orally active vasopressin V1a receptor antagonist, SRX251, selectively blocks aggressive behavior. Pharmacology Biochemistry and Behavior, 83(2), 169-174.
Amsden, G. W. "Anti-inflammatory effects of macrolides" an underappreciated benefit in the treatment of community-acquired respiratory tract infections and chronic inflammatory pulmonary conditions?. Journal of Antimicrobial Chemotherapy 55.1 (2005): 10-21.

de Jong, J. T., et al. "[Large-scale, acute, bacterial gastroenteritis caused by the enterotoxin of *Staphylococcus aureus* after a barbecue]." Nederlands tijdschrift voor geneeskunde 148.43 (2004): 2136-2140.
Raj, Pushker. "Pathogenesis and laboratory diagnosis of *Escherichia coli*" associated enteritis. Clinical microbiology Newsletter 15.12 (1993): 89-93.
Ikeue, T., et al. "[Pneumonia caused by Nocardia nova]." Nihon Kokyuki Gakkai zasshi=the journal of the Japanese Respiratory Society 39.7 (2001): 492-497.
Byrn, S., Pfeiffer, R., Ganey, M., Hoiberg, C., & Poochikian, G. (1995). Pharmaceutical solids: a strategic approach to regulatory considerations. Pharmaceutical research, 12(7), 945-954.
Thakkar, Shyam, and Radheshyam Agrawal. "A case of *Staphylococcus aureus* enterocolitis: a rare entity." Gastroenterology & hepatology 6.2 (2010): 115-117.
Wain, Harry, and Paul A. Blackstone. "Staphylococcal Gastroenteritis." The American journal of digestive diseases 1.10 (1956): 424.
Boyce, Thomas G., "Staphylococcal Food Poisoning," Merck Manuals (2015) 2 pages.
Lv Yang et al., "Polymorphic Drugs." Oct. 31, 2009, pp. 110-111.
Le Loir, Yves, Florence Baron, and Michel Gautier. "*Staphylococcus aureus* and food poisoning." Genet Mol Res 2.1 (2003): 63-76.
Brittain HG editor "Polymorphism in pharmaceutical solids", Chapter 1, p. 1-10 (Grant DJW) and Chapter 5, p. 183-226 (1999).
Graeme, A. O'May, Nigel Reynolds, and George T. Macfarlane. "Effect of pH on an in vitro model of gastric microbiota in enteral nutrition patients." Applied and environmental microbiology 71.8 (2005): 4777-4783.
Cotter, Paul D., and Colin Hill. "Surviving the acid test: responses of gram-positive bacteria to low pH." Microbiology and Molecular Biology Reviews 67.3 (2003): 429-453.
Wain, Harry, and Paul A. Blackstone. "Staphylococcal Gastroenteritis." The American journal of digestive diseases 1.10 (1956): 424-429.
Lyczak, J. B., Cannon, C. L., & Pier, G. B. (2002). Lung infections associated with cystic fibrosis. Clinical microbiology reviews, 15(2), 194-222.
Denis, Alexis, et al. "Synthesis and antibacterial activity of HMR 3647 a new ketolide highly potent against erythromycin-resistant and susceptible pathogens." Bioorganic & medicinal chemistry letters 9.21 (1999): 3075-3080.
Bryskier, A. "Ketolides telithromycin, an example of a new class of antibacterial agents." Clinical Microbiology and Infection 6.12 (2000): 661-669.
Morimoto, Shigeo, et al. "Chemical modification of erythromycins. I. Synthesis and antibacterial activity of 6-O-methylerythromycins A." The Journal of antibiotics 37.2 (1984): 187-189.
Hällgren, Anita, et al. "Antimicrobial susceptibility patterns of enterococci in intensive care units in Sweden evaluated by different MIC breakpoint systems." Journal of Antimicrobial Chemotherapy 48.1 (2001): 53-62.
Fernandes, P., et al. Intravenous Formulation of Solithromycin, a Painless Macrolide Antibiotic in a Rabbit Intravenous Injection Model, 2011, 5 pages.

\* cited by examiner

METHODS FOR TREATING MALARIA, TUBERCULOSIS AND MAC DISEASES

CROSS-REFERENCE TO RELATED APPLICATIONS

This application is a U.S. national application under 37 C.F.R. §371(b) of International Application Serial No. PCT/US2010/048540 filed Sep. 10, 2010, which claims priority under 35 U.S.C. §119(e) to U.S. Provisional Application No. 61/241,258, filed Sep. 10, 2009, which is expressly incorporated by reference herein.

TECHNICAL FIELD

The invention described herein pertains to the treatment of various diseases using fluoroketolides. In particular, the invention described herein pertains to the treatment of *M. avium*, tuberculosis, and malaria

BACKGROUND AND SUMMARY OF THE INVENTION

Malaria is one of the most common infectious diseases and an enormous public health problem. The disease is caused by protozoan parasites of the genus *Plasmodium*, including the most serious form of the disease caused by *Plasmodium falciparum*. Malaria is also caused by *Plasmodium berghei*. Although some are under development, no vaccine is currently available for malaria that provides a high level of protection; preventive drugs must be taken continuously to reduce the risk of infection. These prophylactic drug treatments are often too expensive for most people living in endemic areas. Malaria infections are often treated through the use of antimalarial drugs, such as quinine or artemisinin derivatives. However, the parasites have evolved to be resistant to many of these drugs. Therefore, in some areas of the world, only a few drugs remain as effective treatments for malaria.

Tuberculosis (abbreviated TB for *tubercle bacillus*) is a common and often deadly infectious disease caused by mycobacteria. In humans, TB is caused mainly by *Mycobacterium tuberculosis*. One-third of the world's current population has been infected with *M. tuberculosis*, and new infections occur at a rate of one per second. The proportion of people in the general population who become sick with tuberculosis each year is stable or falling worldwide but, because of population growth, the absolute number of new cases is still increasing. Compounding the impact of this disease is the emergence of resistant strains of TB.

*Mycobacterium avium* complex (MAC) is a group of genetically related bacteria belonging to the genus *Mycobacterium*. It includes *Mycobacterium avium* subspecies *avium* (MAA), *Mycobacterium avium* subspecies *hominis* (MAH), and *Mycobacterium avium* subspecies *paratuberculosis* (MAP). Historically, MAC has also included *Mycobacterium avium* intracellulare (MAI)—a distinct species of bacteria. Treatment involves a combination of anti-tuberculosis antibiotics, which include:Rifampicin, Rifabutin, Ciprofloxacin, Amikacin, Ethambutol, Streptomycin, Clarithromycin, and Azithromycin. Resistance to current therapies is also an issue related to MAC. *M. avium* complex (MAC) infection is a serious health concern for AIDS patients. Standard treatment regimens consist of clarithromycin (CLA), ethambutol and a rifamycin. Treatment failure has been reported. Without being bound by theory, it is believed herein that the failure may be due to the emergence of CLA-resistance.

*M. avium* complex (MAC) infection is a serious health concern for patients living with AIDS, who numbered an estimated 34.4 million people world-wide in 2008. MAC is the causative agent for more than 90% of the non-tuberculous mycobacterial infections in these patients. Standard treatment regimens consist of clarithromycin (CLA), ethambutol and a rifamycin. Though macrolide antibiotics are known to be useful for treating infections such as respiratory tract and soft tissue infections, macrolides have been reported to have poor activity against these diseases.

It has been surprisingly discovered that fluoroketolide macrolides, such as those of the formula I are useful against the infectious pathogens *mycobacterium avium* complex, *mycobacterium tuberculosis, plasmodium falcium*, Narcadia, and *plasmodium berghei*, and diseases caused by those pathogenic organisms, including but not limited to tuberculosis, malaria, including severe malaria and chronic malaria, MAC diseases, such as Hot Tub Lung, Lady Windermere syndrome, and diseases present in immuno-compromised patients, such as senior citizens and those suffering from HIV or cystic fibrosis, and the like.

Described herein are compounds, compositions, formulations, and methods for treating patients with *mycobacterium avium* complex, *mycobacterium tuberculosis, plasmodium falcium*, or *plasmodium berghei*, infection. The compositions, formulations, and methods include a therapeutically effective amount of a macrolide and/or ketolide compound described herein.

In one illustrative embodiment of the invention, compounds, compositions, formulations, and methods are described herein for treating patients with MAC infections, including immunocompromised patients, such as patients with HIV, with MAC infections. In another embodiment, compounds, compositions, formulations, and methods are described herein for treating patients with MAC infections that are caused at least in part by macrolide resistant organisms, including MAC infections caused at least in part by CLA-resistant organisms. The compositions and formulations include a therapeutically effective amount of one or more compounds and/or compositions described herein. The methods include the step of administering a therapeutically effective amount of one or more compounds and/or compositions described herein to the patient.

In another embodiment, compounds, compositions, formulations, and methods are described herein for treating patients with malaria. In another embodiment, compounds, compositions, formulations, and methods are described herein for prophylactically treating patients with malaria. In another embodiment, compounds, compositions, formulations, and methods are described herein for treating patients with malaria caused at least in part by resistant organisms, including resistant *P. vivax, P. falciparum*, and/or caused at least in part by macrolide resistant organisms, such as azithromycin-resistant organisms. The compositions and formulations include a therapeutically effective amount of one or more compounds and/or compositions described herein. The methods include the step of administering a therapeutically effective amount of one or more compounds and/or compositions described herein to the patient.

In another embodiment, compounds, compositions, formulations, and methods are described herein for treating patients with tuberculosis. In another embodiment, compounds, compositions, formulations, and methods are described herein for treating patients with tuberculosis that are caused at least in part by macrolide resistant organisms, including XRD tuberculosis. In another embodiment, compounds, compositions, formulations, and methods are described herein for treating patients with dormant forms of tuberculosis. The compositions and formulations include a therapeutically effective amount of one or more compounds and/or compositions described herein. The methods include the step of administering a therapeutically effective amount of one or more compounds and/or compositions described herein to the patient.

In another embodiment, compounds, compositions, formulations, and methods are described herein for treating patients with pulmonary nocardiosis, including immunocompromised patients, such as patients with HIV, with nocardiosis. In another embodiment, compounds, compositions, formulations, and methods are described herein for treating patients with pulmonary nocardiosis. In another embodiment, compounds, compositions, formulations, and methods are described herein for treating patients with cutaneous nocardiosis. The methods include the step of administering a therapeutically effective amount of one or more compounds and/or compositions described herein to the patient. The compositions and formulations include a therapeutically effective amount of one or more compounds and/or compositions described herein.

DETAILED DESCRIPTION

In another embodiment, methods for treating patients that are need of relief from MAC infections and related diseases, are described herein. In another embodiment, methods for treating immunocompromised patients that are need of relief from MAC infections and related diseases, are described herein. In another embodiment, methods for treating patients suffering from HIV, AIDS and/or AIDS related diseases are described herein. In another embodiment, methods for treating patients suffering from cystic fibrosis (CF) and in need of relief from MAC infections and related diseases, are described herein. Without being bound by theory, it is believed that mycoplama infection in immunocompromised patients, such as those suffering from CF or HIV disease may represent recent acquisition rather than latent infection reactivating, the latter of which may be the case in other opportunistic infections in immunocompromised patients. It is to be understood that the methods described herein may be used in conjunction with other treatments used in patients with HIV, including but not limited to highly active antiretroviral therapy (HAART). It is understood that CF may be exacerbated by certain infections, such as *Mycobacterium avium* complex (MAC) which can cause further lung damage and does not respond to common antibiotics.

In another embodiment, methods for treating malaria are described herein. It is to be understood that the methods and compositions described herein may be used to treat existing disease or alternatively to prophylactically treat patients at risk of contracting malaria. It is also to be understood that the methods described herein may be used to treat malaria caused by one or more organisms that are resistant to current treatments, such as artemisinin, artesunate, and the like.

In another embodiment, methods for treating tuberculosis and related diseases are described herein. Without being bound by theory, it is believed herein that the activity observed with the compounds described herein may be at least in part due to the intracellular accumulation of the compounds, and/or the bactericidal activity of the compounds. It is appreciated that antimicrobial compounds are generally considered to be bactericidal when the MBC is about four times the MIC or less. Illustratively, MBC can be determined from broth dilution MIC tests by subculturing to agar media without antibiotics. Compounds described herein are bactericidal.

In another embodiment, compounds described herein are useful against replicating and dormant *Mycobacterium tuberculosis*. It has been reported that other macrolides, such as clarithromycin, generally show only weak in vitro activity (MIC 8 µg/mL) and in vivo activity against *M. tuberculosis*, and are therefore used in multi-drug resistant tuberculosis where therapeutic options are limited. Compounds described herein are useful in treating diseases caused at least in part by *M. tuberculosis*, including diseases caused at least in part by resistant strains of *M. tuberculosis*. Without being bound by theory, it is believed herein that the efficacy in treating diseases caused at least in part by *M. tuberculosis* may be due at least in part to the intracellular activity and accumulation of compounds described herein. In addition, compounds described herein are efficacious against dormant forms of *M. tuberculosis*. Without being bound by theory, it is believed herein that activity against dormant forms may prevent the reoccurrence of tuberculosis observed with other treatment protocols.

In another embodiment, compounds described herein are bactericidal against isolates of *Mycobacterium avium*, where bactericidal activity is generally considered when the MBC is about 2 µg/mL or less. It has been reported that macrolides and ketolides are not generally bactericidal, including not bactericidal against isolates of *M. avium*.

In another embodiment, compounds described herein show in vitro activity against *Plasmodium falciparum* and in vivo activity equivalent to artemisinin against *Plasmodium berghei*. It is appreciated that compounds described herein may be active against resistant strains of *P. falciparum* and *P. berghei*, including artesunate resistant strains. Without being bound by theory, it is believed herein that the in vivo efficacy in treating malaria may be due at least in part to the intracellular activity and accumulation of compounds described herein.

In one illustrative embodiment, the compositions, formulations, and methods described herein include one more compounds of formula I:

(I)

and pharmaceutically acceptable salts thereof, wherein:
$R_{10}$ is hydrogen or a prodrug group;
X is H; and Y is $OR_7$; where $R_7$ is a monosaccharide or disaccharide, alkyl, aryl, heteroaryl, acyl-, or —C(O)—$NR_8R_9$, where $R_8$ and $R_9$ are each independently selected from the group consisting of hydrogen, hydroxy, alkyl, aralkyl, alkylaryl, heteroalkyl, aryl, heteroaryl, alkoxy, dimethylaminoalkyl, acyl, sulfonyl, ureido, and carbamoyl; or X and Y are taken together with the attached carbon to form carbonyl;

V is —C(O)—, —C(=NR$_{11}$)—, —CH(NR$_{12}$, R$_{13}$)—, or —N(R$_{14}$)CH$_2$—, where N(R$_{14}$) is attached to the C-10 carbon; wherein R$_{11}$ is hydroxy or alkoxy, R$_{12}$ and R$_{13}$ are each independently selected from the group consisting of hydrogen, hydroxy, akyl, aralkyl, alkylaryl, alkoxy, heteroalkyl, aryl, heteroaryl, dimethylaminoalkyl, acyl, sulfonyl, ureido, and carbamoyl; R$_{14}$ is hydrogen, hydroxy, alkyl, aralkyl, alkylaryl, alkoxy, heteroalkyl, aryl, heteroaryl, dimethylaminoalkyl, acyl, sulfonyl, ureido, or carbamoyl;

W is H, F, Cl, Br, I, or OH;

A is —CH$_2$—, —C(O)—, —C(O)O—, —C(O)NH—, —S(O)$_2$—, —S(O)$_2$NH—, —C(O)NHS(O)$_2$—;

B is —(CH$_2$)$_n$— where n is an integer ranging from 0-10, or B is an unsaturated carbon chain of 2-10 carbons; and C is hydrogen, hydroxy, acyl, acyloxy, sulfonyl, ureido, or carbamoyl, or alkyl, aralkyl, alkylaryl, alkoxy, heteroalkyl, aryl, heteroaryl, aminoaryl, aminoheteroaryl, or alkylaminoaryl, each of which is optionally substituted.

In one variation of the foregoing embodiment of formula (I), R$^{10}$ is H. In another variation, X is H; and Y is OR$_7$; where R$_7$ is a monosaccharide or disaccharide. In another variation, X is H; and Y is OR$_7$; where R$_7$ is a monosaccharide. In another variation, X is H; and Y is cladinose. In another variation, X and Y are taken together with the attached carbon to form carbonyl In another variation, V is C(O). In another variation, W is H or F. In another variation, W is F. In another variation, A is CH$_2$. In another variation, B is —(CH$_2$)$_n$— where n is an integer ranging from 0-10. In another variation, B is —(CH$_2$)$_n$— where n is an integer ranging from 3-5. In another variation, C is aryl, heteroaryl, aminoaryl, aminoheteroaryl, or alkylaminoaryl, each of which is optionally substituted. In another variation, C is aminoaryl or aminoheteroaryl, each of which is optionally substituted. It is to be understood that each of the foregoing variations may be combined without limitation, and serve as an explicit description of other illustrative embodiments of the invention. For example, in another embodiment of formula (I), R$^{10}$ is H, X and Y are taken together with the attached carbon to form carbonyl, W is F, and C is aminoaryl or aminoheteroaryl.

In another embodiment, the compositions, formulations, and methods described herein include a compound of the formula also referred to as CEM-101 or solithromycin, or a pharmaceutically acceptable salt thereof.

The compounds described herein may be prepared as described herein, or according to US Patent Application Publication No. 2006/0100164 and in U.S. Provisional Application Ser. No. 60/982,446, the disclosures of which are incorporated herein by reference in their entirety.

The term "patient" refers to mammals, including humans, companion animals, and livestock animals. A patient in need is a patient who is infected with or exposed to one or more of the listed infectious pathogens. A patient who is immunocompromised is one who is immunodeficient wherein the patient's immune system's ability to fight infectious disease is compromised or entirely absent. Most cases of immunodeficiency are acquired ("secondary"), such as those patients with HIV or taking immunosuppressing drugs, but some people are born with defects in the immune system, or primary immunodeficiency. Transplant patients take medications to suppress their immune system as an anti-rejection measure, as do some patients suffering from an over-active immune system. An immunocompromised person may be particularly vulnerable to opportunistic infections, in addition to normal infections that could affect everyone.

The term "inhibiting" includes its generally accepted meaning which includes prohibiting, preventing, restraining, and slowing, stopping or reversing progression, severity or a resultant symptom. As such, the present method includes both medical therapeutic and/or prophylactic administration, as appropriate.

"Pharmaceutically acceptable" as used in this application, for example with reference to salts, hydrates, solvates, esters, and formulation components such as carriers, means substantially non-deleterious to the recipient patient, and includes "veterinarily acceptable," and thus includes both human and animal applications independently.

Pharmaceutically acceptable salts, and common methodology for preparing them are known in the art. See, e.g., P. Stahl, et al., Handbook of Pharmaceutical Salts: Properties, Selection And Use, (VCHA/Wiley-VCH, 2002); S. M. Berge, et al., "Pharmaceutical Salts," *Journal of Pharmaceutical Sciences*, Vol. 66, No. 1, January 1977. Examples of salts include, but are not limited to, salts formed by standard reactions with both organic and inorganic acids, such as sulfuric, hydrochloric, phosphoric, acetic, succinic, citric, lactic, maleic, fumaric, cholic, pamoic, mucic, glutamic, camphoric, glutaric, glycolic, phthalic, tartaric, formic, lauric, stearic, salicylic, methanesulfonic, benzenesulfonic, sorbic, picric, benzoic, cinnamic and like acids.

Compounds are illustratively formulated as pharmaceutical compositions administered by a variety of routes including the oral, rectal, transdermal, subcutaneous, topical, intravenous, intramuscular or intranasal routes. See, e.g., Remington: The Science And Practice Of Pharmacy (A. Gennaro, et al., eds., 19$^{th}$ ed., Mack Publishing Co, 1995).

The formulations described herein include a therapeutically effective amount of one of more compounds described herein, and optionally include one or more carriers, diluents, or excipients, or a combination thereof.

The term "carrier" is used herein to describe any ingredient other than the active components in a formulation. The choice of carrier will to a large extent depend on factors such as the particular mode of administration, the effect of the carrier on solubility and stability, and the nature of the dosage form.

The term "therapeutically effective amount" as used herein, refers to that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated. In one aspect, the therapeutically effective amount is that which may treat or alleviate the disease or symptoms of the disease at a reasonable benefit/risk ratio applicable to any medical treatment. However, it is to be understood that the total daily usage of the compounds and compositions described herein may be decided by the attending physician within the scope of sound medical judgment. The specific therapeutically-effective dose level for any particular patient will depend upon a variety of factors, including the disorder being treated and the severity of the disorder; activity of the specific compound employed; the specific composition employed; the age, body weight, general health, gender and diet of the patient: the time of administration, route of administration, and rate of excretion of the specific compound employed; the duration of the treatment; drugs used in combination or coincidentally with the specific compound employed; and like factors well known to the researcher, veterinarian, medical doctor or other clinician of ordinary skill As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

The term "administering" as used herein includes all means of introducing the compounds and compositions described herein to the patient, including, but are not limited to, oral (po), intravenous (iv), intramuscular (im), subcutaneous (sc), transdermal, inhalation, buccal, ocular, sublingual, vaginal, rectal, and the like. The compounds and compositions described herein may be administered in unit dosage forms and/or formulations containing conventional nontoxic pharmaceutically-acceptable carriers, adjuvants, and vehicles.

Illustratively, administering includes local use, such as when administered locally to the site of disease, injury, or defect. Illustrative local administration may be performed during open surgery, or other procedures when the site of disease, injury, or defect is accessible. Alternatively, local administration may be performed using parenteral delivery where the compound or compositions described herein are deposited locally to the site without general distribution to multiple other non-target sites in the patient being treated. It is further appreciated that local administration may be directly in the injury site, or locally in the surrounding tissue. Similar variations regarding local delivery to particular tissue types, such as organs, and the like, are also described herein. Illustratively, compounds may be administered directly to the nervous system including, but not limited to, intracerebral, intraventricular, intracerebroventricular, intrathecal, intracisternal, intraspinal and/or peri-spinal routes of administration by delivery via intracranial or intravertebral needles and/or catheters with or without pump devices.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic carbocyclic groups, each of which may be optionally substituted. Illustrative aromatic carbocyclic groups described herein include, but are not limited to, phenyl, naphthyl, and the like. As used herein, the term "heteroaryl" includes monocyclic and polycyclic aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

The term "alkoxy," alone or in combination, refers to an alkyl ether radical, alkyl-O—, wherein the term alkyl is defined as above. Examples of alkoxy radicals include methoxy, ethoxy, n-propoxy, isopropoxy, n-butoxy, iso-butoxy, sec-butoxy, tert-butoxy and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "sulfonyl or a derivative thereof" includes $SO_3H$ and salts thereof, and esters and amides thereof.

As used herein, monosaccharides are generally single polyhydroxy aldehyde or ketone unit. Representative monosaccharides include, hexoses such as D-glucose, D-mannose, D-xylose, D-galactose, L-fucose, and the like; pentoses such as D-ribose or D-arabinose and ketoses such as D-ribulose or D-fructose. "Disaccharides" contain two monosaccharide units joined by a glycosidic linkage. Disaccharides include, for example, sucrose, lactose, maltose, cellobiose, and the like. Oligosaccharides typically contain from 2 to 10 monosaccharide units joined by glycosidic linkages.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical —$(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl)alkylcarbonylaminoalkyl, cyano, and nitro; or $Z^X$ is selected from —$CO_2R^4$ and —$CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —NR$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy)prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, $(C_3-C_{20})$alkanoyl; halo-$(C_3-C_{20})$alkanoyl; $(C_3-C_{20})$alkenoyl; $(C_4-C_7)$cycloalkanoyl; $(C_3-C_6)$-cycloalkyl$(C_2-C_{16})$alkanoyl; optionally substituted aroyl, such as unsubstituted aroyl or aroyl substituted by 1 to 3 substituents selected from the group consisting of halogen, cyano, trifluoromethanesulphonyloxy, $(C_1-C_3)$alkyl and $(C_1-C_3)$alkoxy, each of which is optionally further substituted with one or more of 1 to 3 halogen atoms; optionally substituted aryl$(C_2-C_{16})$alkanoyl, such as the aryl radical being unsubstituted or substituted by 1 to 3 substituents selected from the group consisting of halogen, $(C_1-C_3)$alkyl and $(C_1-C_3)$alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, $(C_1-C_3)$alkyl, and $(C_1-C_3)$alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

EXAMPLES

The following examples further illustrate specific embodiments of the invention; however, the following illustrative examples should not be interpreted in any way to are to limit invention.

EXAMPLE. Comparison of the in vitro activity of CEM-101 to CLA against both CLA-susceptible (S) and resistant (R) isolates of MAC as well as comparing the in vivo activity against a CLA-S isolate.

Clarithromycin was dissolved in dimethyl sulfoxide (DMSO) at a final concentration of 1 mg/ml. CEM-101 was dissolved in water with glacial acetic acid (added until dissolved) at a final concentration of 1 mg/ml. CEM-101 was filter sterilized by passage through a 0.22 μm-pore sized membrane filter. All drugs were aliquoted and frozen at −20° C. until use.

Isolates. Clinical isolates were obtained from SUNY Upstate Medical University and MAC 101 (ATCC 700898) and MAC LPR (ATCC 49601) were obtained from ATCC (Manassas, Va.). The isolates were grown in modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md.) and 0.05% Tween 80 for 5-10 days on a rotary shaker at 37° C. The culture was diluted to 10 Klett units (equivalent to 5×10$^7$ colony forming units (CFU)) per ml (Photoelectric Colorimeter; Manostat Corp., New York, N.Y.). The culture was frozen at −70° C. until use. On the day of testing the culture was thawed and diluted to a final concentration of 1.25×10$^5$ CFU/ml. The final inoculum size was determined by titration, in duplicate, on 7H10 agar plates supplemented with 10% OADC enrichment (BBL Microbiology Systems, Cockeysville, Md.). The plates were incubated at 37° C. in ambient air for 14 days.

Broth dilution method. Polystyrene 96 well round-bottom microtiter plates (Corning Inc., Corning, N.Y.) were prepared by adding 50 μl of modified 7H10 broth with serial dilutions of the drugs to be tested using a multichannel electronic pipetter. To each well 50 μl of the appropriate mycobacterial cell suspension was added to yield a final concentration of about 6×10$^4$ CFU/ml (range for various isolates tested was 2.2×10$^6$ CFU/ml-7.3×10$^4$ CFU/ml). Each drug was tested in duplicate. The microtiter plates were covered with SealPlate adhesive sealing film (Excel Scientific, Wrightwood, Calif.) and incubated at 37° C. in ambient air for about 5-7 days prior to reading. The MIC was defined as the lowest concentration of antimicrobial agent yielding no visible turbidity.

In vivo. Mice. Six-week old female C57BL/6 mice were purchased from Jackson Laboratories, Bar Harbor, Me. and were maintained within the Syracuse VA Medical Center's Veterinary Medical Unit, Syracuse, N.Y. All animal procedures were approved by the Subcommittee for Animal Studies (SAS). Mice were housed in micro-isolator cages (lab products inc, Maywood, N.J.) and maintained with water and Prolab RMH 3000 rodent chow (Purina, St. Louis, Mo.).

Drugs. On the day of treatment CLA was dissolved in 20% ethanol followed by 5 minutes of sonication and was dosed at a concentration of 200 mg/kg in a 0.2 ml volume (actual ethanol concentration was 4%). CEM-101 was dissolved in 0.5% methyl cellulose followed by 5 minutes of sonication and was dosed at 200, 100, 50 or 25 mg/kg.

Isolate. M. avium LPR ATCC 49601 was grown in modified 7H10 broth (pH 6.6; 7H10 agar formulation with agar and malachite green omitted) with 10% OADC (oleic acid, albumin, dextrose, catalase) enrichment (BBL Microbiology Systems, Cockeysville, Md.) and 0.05% Tween 80 for 5-10 days on a rotary shaker at 37° C. The culture was diluted to 100 Klett units (equivalent to $5 \times 10^8$ colony forming units (CFU)) per ml (Photoelectric Colorimeter; Manostat Corp., New York, N.Y.). The final inoculum size was determined by titration, in triplicate, on 7H10 agar plates supplemented with 10% OADC enrichment (BBL Microbiology Systems, Cockeysville, Md.). The plates were incubated at 37° C. in ambient air for 14 days.

Infection study. Mice were infected intranasally with $2.4 \times 10^7$ CFU of M. avium LPR. Mice were randomly assigned to 7 groups of 6 mice: Early Control (EC), Late Control (LC), CLA 200 mg/kg, CEM-101 200 mg/kg, CEM-101 100 mg/kg, CEM-101 50 mg/kg, CEM-101 25 mg/kg. One week post-infection mice were treated with the above agents orally by gavage in a 0.2 ml volume 5 days/week for 4 weeks. The EC group was euthanized at the initiation of therapy to determine the infection load. An LC group was euthanized at the end of treatment to determine the level of infection without therapy. Mice were sacrificed by CO2 inhalation after the completion of therapy. Right lungs and spleens were aseptically removed and ground in a sealed tissue homogenizer (IdeaWorks! Laboratory Devices, Syracuse, N.Y.). The number of viable organisms was determined by serial dilution and titration on 7H10 agar plates. Plates were incubated at 37° C. in ambient air for 14 days prior to counting.

Statistical evaluation. The viable cell counts were converted to log 10 and then evaluated by ANOVA. Post-hoc analyses were conducted using Tukey's Multiple Comparisons Test. Statistical significance was accepted with P value of less than 0.05.

The range of MICs for the CLA-S strains against CLA was 0.125 to 8 ηg/ml while the MICs for CEM-101 ranged from 0.125 to 16 µg/ml, The MICs of CLA against the CLA-R isolates ranged from 32 to 128 µg/ml while the range for CEM-101 was 8 to 16 g/ml. MAC LPR was the control strain.

TABLE

MIC of Clarithromycin (CLA) and CEM-101 versus M. avium complex.

| Isolate Mycobacterium avium | CEM 101 MIC µg/ml | Clarithromycin MIC µg/ml | Clarithromycin Resistant—R or Susceptible—S |
|---|---|---|---|
| MAC LPR | 8 | | |
| MAC 1408 | 0.25 | 0.25 | S |
| MAC 9141 | 1 | 0.25 | S |
| MAC SMT | 0.125 | 0.25 | S |
| MAC FAR | 0.125 | 0.125 | S |
| MAC KZL | 8 | 1 | S |
| MAC GRL | 8 | 2 | S |
| MAC TRY | 8 | 0.5 | S |
| MAC 101 | 0.25 | 0.125 | S |
| MAC KAL | 16 | 8 | S |
| MAC TEL | 8 | 2 | S |
| MAC 3404.4 | 0.125 | 0.125 | S |

TABLE-continued

MIC of Clarithromycin (CLA) and CEM-101 versus M. avium complex.

| Isolate Mycobacterium avium | CEM 101 MIC µg/ml | Clarithromycin MIC µg/ml | Clarithromycin Resistant—R or Susceptible—S |
|---|---|---|---|
| MAC 103 | 8 | 64 | R |
| MAC Pry | 8 | 64 | R |
| MAC 320 | 8 | 64 | R |
| MAC 216 | 8 | 32 | R |
| MAC 643 | 8 | 64 | R |
| MAC 309 | 8 | 64 | R |
| MAC 621 | 16 | 128 | R |
| MAC 623 | 16 | 64 | R |
| MAC 110 | 8 | 64 | R |
| MAC 224 | 8 | 128 | R |
| MAC 625 | 8 | 64 | R |
| MAC 108 | 8 | 64 | R |

Figure 1:
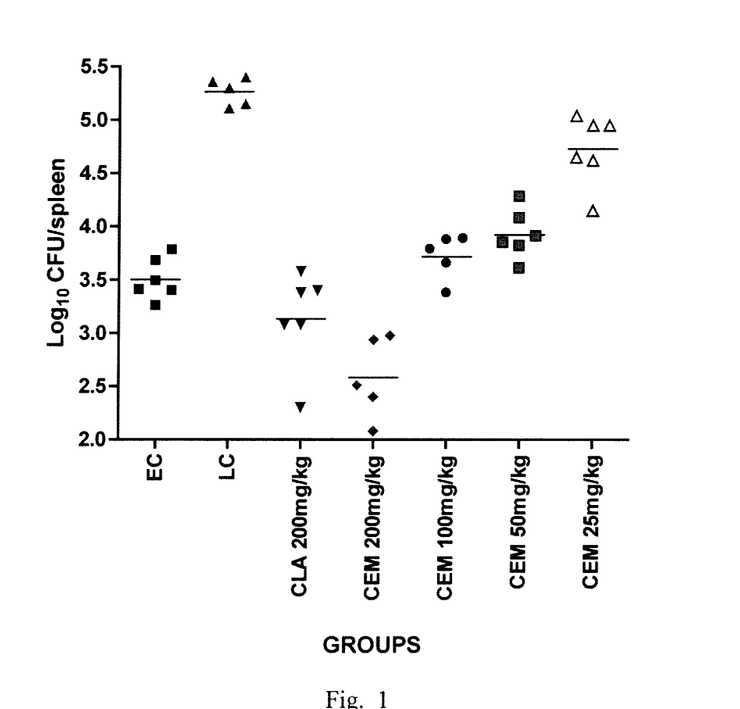
FIG. 1 shows CFU recovered from the spleens of mice infected with MAC LPR, where CLA is clarithromycin and CEM is CEM-101.
Figure 2:
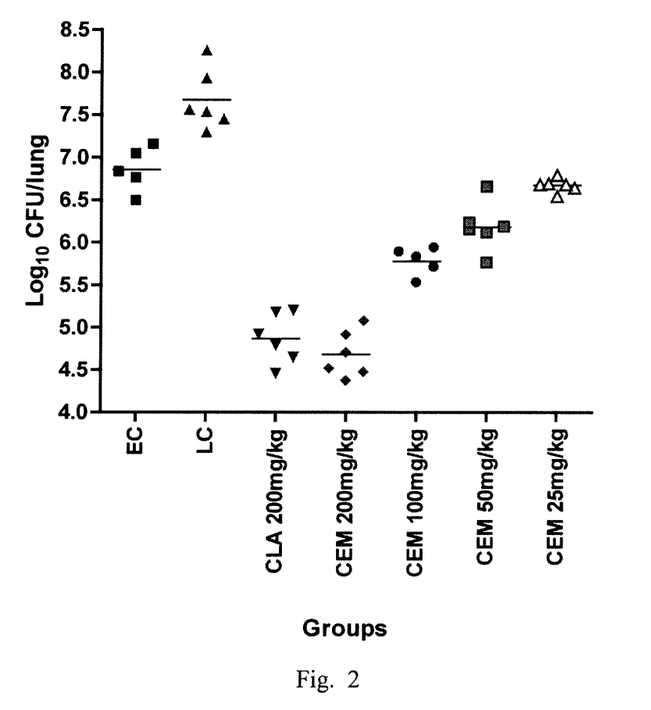
FIG. 2 shows CFU recovered from the lungs of mice infected with MAC LPR, where CLA is clarithromycin and CEM is CEM-101.

There was a significant increase in growth of MAC LRP in the spleens and lungs of untreated mice over the 4 week treatment period (P<0.05). The reduction in growth of MAC LPR in the spleens and lungs was significant for mice receiving CLA at 200 mg/kg and CEM-101 at 200, 100 and 50 mg/kg compared to the late controls (P<0.05), but not for CEM-101 at 25 mg/kg (P>0.05). Although the reduction in CPU of MAC LPR was greater in both the spleens and lungs of mice receiving CEM-101 at 200 mg/kg compared to the CLA 200 mg/kg group it was not statistically significant (P>0.05). There was a dose response of CEM-101 observed in both the spleens and lungs (FIG. 1 and FIG. 2).

CEM-101 had potent in vitro activity against both CLA-R and CLA-S MAC isolates. The range of MICs for CEM-101 was unchanged when comparing the activity between the resistant and susceptible strains. CEM-101 also had potent in vivo activity that was slightly better than CLA against the CLA-S M. avium strain MAC LPR in the murine model of M. avium infection. The standard model was utilized to test the anti-mycobacterial activity of CLA and CEM-101 which includes therapeutic interruptions for 2 days during the weekends.

EXAMPLE. CEM-101 is bactericidal against M. avium and significantly active against M. leprae.

M. avium and M. leprae In Vitro Activity Summary

| Organism | MIC90 (range) (µg/mL) | MBC (range) (µg/mL) |
|---|---|---|
| M. avium (30) | 1 (1) | 2 (2) |
| M. leprae (1) | 0.15 µg/mL reduced viability in axenic cultures (p < 0.001) | |

EXAMPLE. CEM-101 shows potent activity against M. avium, including macrolide-resistant isolates for which comparator macrolides and ketolides were previously reported to have lower activity (≥4-fold less active than CEM-101) (Table 7). CEM-101 is bactericidal for M. avium with an MBC of 2 µg/mL against all strains tested.

TABLE

M. avium In Vitro Activity Summary

| Organism | N | Compound | MIC90 (range) (µg/mL) | MBC (range) (µg/mL) |
|---|---|---|---|---|
| M. avium | 30 | CEM-101 | 1 (1) | 2 (2) |

CEM-101 showed potent activity against *M. avium*, including macrolide-resistant *M. avium*. Published data on other macrolides and ketolides report significantly lower activity than observed in the CEM-101 study (≥4-fold lower) and these agents are not active against clarithromycin- and azithromycin-resistant isolates (Bermudez 2007; Cynamon 2000). Further, CEM-101 was shown to be bactericidal for *M. avium* at the concentrations tested (MBC 2 µg/mL) (Table 4). This is in contrast to a lack of significant bactericidal activity for macrolides, telithromycin, or cethromycin (Bermudez 2001).

In vivo studies are ongoing in mice infected with macrolide-susceptible strain MAC 101.

TABLE

*M. avium* Susceptibility to CEM-101

| Organism | N | Phenotype | Compound | MIC (µg/mL) | Range (µg/mL) | MBC (µg/mL) |
|---|---|---|---|---|---|---|
| *M. avium* | 24 | susceptible | CEM-101 | 1 | 1 | 2 |
|  | 6 | resistant | CEM-101 | 1 | 1 | 2[a] |

[a] MBCs were calculated for 4 of the resistant strains.

EXAMPLE. MIC values (µg/mL) of CEM-101 against clinical XDR strains of *M. tuberculosis* (50 ug/mL highest concentration tested).

| Strain | OB031 | OB062 | OB082 | OB076a | OB076b | OB019 | OB081 | OB005 |
|---|---|---|---|---|---|---|---|---|
| 1 week | 0.049 | — | 0.049 | 0.049 | 0.049 | — | — | 3.125 |
| 2 weeks | 0.78-1.56 | 0.39-0.78 | 0.098 | 0.098 | 0.049 | 1.56 | 12.5 | 12.5 |

The MIC is taken as the concentration that completely prevents all visible growth. The MIC plates were re-read after 2 weeks of growth due to certain slow-growing strains (OB062, OB019, and OB081). Some MICs were also dependent upon the overall number of cells. Strain OB031 initially had an MIC of 0.049 ug/mL but changed after a week (as the cell number increased) to 0.78-1.56 ug/mL.

CEM-101 was also tested against infected macrophages and was very effective against MTb growing inside macrophages. Activity against MTb inside macrophages is based on ATP readouts on MTb released from the infected treated cells at various time points, which were allowed to grow out, which showed a 10-fold decrease in ATP of cells treated with 1 µg/mL CEM-101.

EXAMPLE. In two in vitro experiments against replicating bacteria, CEM-101 was more active than clarithromycin against *Mycobacterium tuberculosis*. CEM 101 is active against dormant *M. tuberculosis* and replicating *M. tuberculosis* CEM-101 was significantly more active against non-replicating *M. tuberculosis*.

TABLE

*M. tuberculosis* In Vitro Activity Summary

| | Replicating Culture | | Non-Replicating Culture |
|---|---|---|---|
| ID | MABA MIC (µM) | Aero RLU (µM) | LORA (µM) |
| CEM-101 | 9.23 | 7.19 | 10.43 |
| | 9.17 | 6.95 | 7.55 |

TABLE-continued

*M. tuberculosis* In Vitro Activity Summary

| | Replicating Culture | | Non-Replicating Culture |
|---|---|---|---|
| ID | MABA MIC (µM) | Aero RLU (µM) | LORA (µM) |
| Clarithromycin | 13.34 | 18.82 | >128 |
| | 14.54 | 22.46 | 43.00 |

MABA: Microplate Alamar Blue Assay; Aero RLU: Relative Light Units under Aerobic conditions; LORA: Low Oxygen Recovery Assay (Anaerobic). Clarithromycin LORA typically >128 µM.

EXAMPLE. CEM-101, unlike clindamycin, was determined to be curative in a murine malarial infection model that assessed activity against *Plasmodium berghei* at the time the mice were sacrificed for testing. Macrolides in general, including telithromycin (MABA MIC 128 µg/mL), have reportedly poor activity against *M. tuberculosis*. Clarithromycin has weak in vitro (MABA MIC 8 µg/mL) and in vivo activity, and is used in multi-drug resistant tuberculosis where therapeutic options are limited. Cethromycin (MABA MIC 4 µg/mL failed to significantly reduce CFU in the lungs of mice following treatment with 100 mg/kg once daily for 3 weeks (Zhu 2008). CEM-101 was more active against replicating *Mycobacterium tuberculosis* and had an even larger differential against non-replicating *M. tuberculosis* (LORA) when compared to clarithromycin (Table 3).

EXAMPLE. CEM-101 activity in vitro. CEM-101 produced variable and slow killing in vitro against *Plasmodium falciparum* in both the 72-hour assay and the 120-hour assay.

TABLE

In Vitro *P. falciparum* Activity in the 72 hour Assay (48 + 24)

| | $IC_{50}$ NF54 | | | |
|---|---|---|---|---|
| Drug | Test 1 | Test 2 | Test 3 | Test 4 |
| CEM-101 | 919 | 1536 | 1487 | 1258 |
| Chloroquine | 4.4 | 5.4 | 4.4 | 4.8 |
| Artesunate | 3.0 | 3.2 | 3.0 | 2.8 |

TABLE

In Vitro *P. falciparum* Activity in the 120 hour Assay (96 + 24)

| | $IC_{50}$ NF54 | | |
|---|---|---|---|
| Drug | Test 1 | Test 2 | Test 3 |
| CEM-101 | <156 | <15 | 2.4 |
| Clindamycin | <7.8 | 5.3 | 5.3 |
| Chloroquine | 4.6 | 4.6 | 4.7 |
| Artesunate | 4.2 | 3.9 | 3.3 |

In vivo antimalarial activity was demonstrated in mice intravenously infected with *P. berghei* strain ANKA. Control mice survived an average of 4 days following infection.

EXAMPLE. CEM-101 activity in infected mice. In vivo antimalarial activity was demonstrated in mice intravenously infected with *P. berghei* strain ANKA. Control mice survived an average of 4 days following infection. CEM-101 treatment at 4×100 mg/kg resulted in cure, which was defined as survival on Day 30 with no detectable parasites. Clindamycin at the same dose resulted in survival increasing only to Day 15. Artesunate in this murine malaria model requires the same oral dose (4×100 mg/kg) to result in a cure.

TABLE

In Vivo Antimalarial Activity against *P. berghei* (GFP MRA-865)

| | 1 × 100 mg/kg (oral) | | 4 × 100 mg/kg (oral) | | |
|---|---|---|---|---|---|
| Compound | Activity (%) | Survival (days) | Activity (%) | Survival[a] (days) | Cure (%) |
| Untreated Control | — | 4 | — | 4 | 0 |
| CEM-101 (DMSO) | 80.05 | 15.7 | 99.79 | 30.0 | 100 |
| CEM-101 (HMPC) | 81.45 | 12.7 | 99.79 | 30.0 | 100 |
| Azithromycin (DMSO) | 70.39 | 14.0 | 99.11 | 30.0 | 0 |
| Azithromycin (HMPC) | 65.19 | 14.0 | 99.13 | 24.0 | 0 |
| Clindamycin (DMSO) | 78.79 | 7.0 | 99.75 | 18.3 | 0 |
| Clindamycin (HMPC) | 79.06 | 7.3 | 99.59 | 20.0 | 0 |

[a]Surviving mice were sacrificed on Day 31 to determine the presence or absence of parasites.

It is observed that the blood from CEM-101 treated animals is parasite free, while that from azithromycin treated animals is not, as shown in the following table.

| Substances | Dosages mg/kg: 4× | Route | Visual Observation | Parasitized RBC in one drop of blood (made by microscope) | | |
|---|---|---|---|---|---|---|
| CEM-101 | 100 | DMSO | p.o. | neg | 0 | 0 | 0 |
| CEM-101 | 100 | HPMC | p.o. | neg | 0 | 0 | 0 |
| | | | | Parasitized RBC over 100 (made by FACS) | | |
| Azithromycin | 100 | DMSO | p.o. | pos | 34.32 | 2.20 | 36.31 |
| Azithromycin | 100 | HPMC | p.o. | pos | X | 74.04 | X |

EXAMPLE. CEM-101 activity as prophylactic. Mice inoculated IV with 0.1 ml, 100,000 *P. berghei* ANKA sporozoites from mosquitoes. Drug administered Day −1, 0 and 1, Once daily for 3 days.

| Drug # | Doses | Route | Day of death | Activity |
|---|---|---|---|---|
| None | 0 | SC | 6 | N/A |
| CEM101 | 160 | | — | Complete curative |
| | 120 | | — | Complete curative |
| | 80 | | — | Complete curative |
| | 40 | | — | Complete curative |
| None | 0 | PO | 6-7 | N/A |
| CEM101 | 160 | | — | Complete curative |
| | 120 | | — | Complete curative (3 mice) |
| | 80 | | — | Clearance with recrudescence (2 mice) Complete curative (3 mice) Clearance with recrudescence (2 mice) |
| | 40 | | — | Clearance with recrudescence |

CEM-101 is active in vitro against *P. falciparum* in extended incubation assays which measure the potency of inhibitors that demonstrate delayed death effects. CEM-101 is also active against blood stages in *P. berghei*-infected mice.

Dose-response for CEM-101 was characterized in both blood stage treatment and causal prophylactic *P. berghei*-infected mice models using 3 day PO or SC dosing. Efficacy was measured by number of mice with delayed parasitemia and mice that were malaria free at day 31. Antimalarial liver stage activity was assessed in mice infected with luciferase expressing *P. berghei* parasites using an in vivo imaging system.

For blood stage infections, the minimum curative SC dose was 40 mg/kg/d×3 days, while 80 mg/kg/d×3 was the minimum active dose for PO route. In the *P. berghei* causal mouse model, CEM-101 was curative at 40 mg/kg/d×3 days with SC or PO dosing. No systemic toxicity was observed with SC or PO dosing as high as 160 mg/kg/d×3 days. No demonstrable antimalarial activity against liver stage parasites was observed by in vivo imaging analysis of luciferase-expressing *P. berghei* with PO dosing at 40 mg/kg/d×3 days. Though drug activity against liver stage parasites could not be measured by in vivo imaging, no blood stage infection was detected in mice dosed as low as 40 mg/kg/d×3 days and the minimum active dose was 20 mg/kg/d×3 days.

CEM-101 shows 100% prophylactic activity in causal mouse malaria models with PO dosing at 40 mg/kg/d×3 days and 3/5 mice remain parasite free at 20 mg/kg/d×3 days. The in vivo imagining analysis of liver stage parasites suggests that CEM-101 does not affect parasite growth at 40 mg/kg/d×3 days. Based on in vitro blood stage drug assays and the mechanism of inhibition of this class of compounds, higher doses of CEM-101 may show demonstrable liver stage activity. These results suggest that CEM 101 demonstrates a delayed death effect; that is, developing liver stage merozoites are effectively non-viable blood stage parasites.

Data indicate that the compounds described herein are useful in prophylaxis and treatment of malaria, including resistant strains of *P. vivax* and/or *P. falciparum*, and including strains resistant to azithromycin. The data also indicate that the compounds described herein may be useful against one or more of Sporozoites, Trophozoites, Merozoites, Hypnozoites, which reportedly have ribosomes in apicoplast and mitochondria. Without being bound by theory, it is believed herein that the activity described herein may result at least in part from the observed activity of the compounds described herein at low pH. It is also believed herein that the activity described herein may result at least in part from the observed intracellular activity of the compounds described herein.

EXAMPLE. In vitro and in vivo activity against different species of *Plasmodium* parasites. CEM-101 was tested against intra-erythrocytic forms of P. falciparum derived from asynchronous cultures of the strain NF544. Parasite growth over 120 h was measured by the incorporation of radiolabelled [$^3$H]hypoxanthine (in hypoxanthine free culture medium) added after 96 h of drug incubation and 24 h prior to the termination of the test. CEM-101 was followed for 120 h. CEM-101 has delayed activity when compared to other agents.

In vitro P. falciparum data for CEM-101 in the 72 h Assay (48+24)

| Drug | IC50 NF54 ng/mL | | | |
|---|---|---|---|---|
| | TEST 1 | TEST 2 | TEST 3 | TEST 4 |
| CEM-101 | 919 | 1536 | 1487 | 1258 |
| Chloroquine | 4.4 | 5.4 | 4.4 | 4.8 |
| Artesunate | 3.0 | 3.2 | 3.0 | 2.8 |

In vitro P. falciparum data for CEM-101 in the 120 h Assay (96+24)

| Drug | IC50 NF54 ng/mL |
|---|---|
| CEM-101 | 2.4 |
| Clindamycin | 5.3 |
| Chloroquine | 4.7 |
| Artesunate | 3.3 |

EXAMPLE. CEM-101 was tested in the murine P. berghei model as described by Vennerstrom et al. Nature 430(7002):900-904 (2004), the disclosure of which is incorporated herein by reference. The data indicate that CEM-101 has equivalent activity to Artesunate in the mouse model. The data indicate that CEM-101 is curative for mouse malaria in the model.

TABLE

In vivo P. berghei antimalarial activity after a single 100 mg dose

| Substances | Dosages mg/kg: 1x | Route | % Activity * | Mouse Survival in Days Avg |
|---|---|---|---|---|
| Clindamycin | 100 | DMSO | p.o. | 78.79 | 7.0 |
| Clindamycin | 100 | HPMC | p.o. | 79.06 | 7.3 |
| CEM-101 | 100 | DMSO | p.o. | 80.05 | 15.7 |
| CEM-101 | 100 | HPMC | p.o. | 81.45 | 12.7 |
| Azithromycin | 100 | DMSO | p.o. | 70.39 | 14.0 |
| Azithromycin | 100 | HPMC | p.o. | 65.19 | 14.0 |
| Control Day 4 | — | — | — | — | 4.0 |

* % Activity is difference of mean infection rate of the untreated control group to the test group- percent.

TABLE

In vivo P. berghei antimalarial activity after 100 mg dose x 4 days

| Substances | Dosages mg/kg: 4x | Route | % Activity | Mouse Survival in Days Avg |
|---|---|---|---|---|
| Clindamycin | 100 | DMSO | p.o. | 99.75 | 18.3 |
| Clindamycin | 100 | HPMC | p.o. | 99.59 | 20.0 |
| CEM-101 | 100 | DMSO | p.o. | 99.79 | 30.0 |
| CEM-101 | 100 | HPMC | p.o. | 99.79 | 30.0 |
| Azithromycin | 100 | DMSO | p.o. | 99.11 | 30.0 |
| Azithromycin | 100 | HPMC | p.o. | 99.13 | 24.0 |
| Control Day 4 | — | — | — | — | 4.0 |

EXAMPLE. CEM101 is active when tested against Azi resistant strain (Fidock).

TABLE

CEM-101: Effect on the P. falciparum lines Dd2 and 7G8 (both multidrug resistant)
Fidock lab - 96 hours

| Line | Run | IC50 nM | Mean IC50 nM | SD |
|---|---|---|---|---|
| Dd2 | 1 | 62.7 | 38.6 | 14.8 |
| Dd2 | 2 | 11.8 | | |
| Dd2 | 3 | 41.2 | | |
| 7G8 | 1 | 16.6 | 18.5 | 5.2 |
| 7G8 | 2 | 10.5 | | |
| 7G8 | 3 | 28.3 | | |
| AZR Dd2-R2 | 1 | 73.2 | 69.1 | 2.5 |
| AZR Dd2-R2 | 2 | 64.5 | | |
| AZR Dd2-R2 | 3 | 69.7 | | |
| AZR 7G8-R1 | 1 | 77.9 | 80.2 | 16.1 |
| AZR 7G8-R1 | 2 | 53.4 | | |
| AZR 7G8-R1 | 3 | 109.1 | | |

EXAMPLE. CEM-101 and Clarithromycin Concentrations in the Heart. After 14-days of daily dosing in monkeys, CEM-101 showed significantly lower levels in the heart than clarithromycin.

EXAMPLE. CEM-101, Telithromycin and Clarithromycin Levels in the Lung. After 14-days of daily dosing in monkeys, CEM-101 showed significantly higher levels in the lung than either clarithromycin or telithromycin.

EXAMPLE. Intracellular activity of CEM-101. Compared to azithromycin, telithromycin, and clarithromycin, CEM-101 showed significantly higher intracellular accumulation. After 24 hours, the intracellular concentration of CEM-101 was more than 2-fold higher than any of azithromycin, clarithromycin, and telithromycin, in decreasing order of ability for intracellular accumulation. CEM-101 intracellular accumulation was dose dependent.

What is claimed is:

1. A method for treating a patient having a *Mycobacterium avium* complex, *Mycobacterium tuberculosis*, *Nocardia*, *Plasmodium falciparum*, or *Plasmodium berghei* infection, the method comprising the step of administering to the patient a therapeutically effective amount of a composition comprising CEM-101 or a pharmaceutically acceptable salt thereof.

2. The method of claim 1 wherein the infection is a *Mycobacterium tuberculosis*, *Plasmodium falciparum*, or *Plasmodium berghei* infection.

3. The method of claim 1 wherein the patient is a human.

4. The method of claim 1 wherein the patient is a human, that is immunocompromised.

5. A method for treating malaria, the method comprising the step of administering to the patient a therapeutically effective amount of a composition comprising CEM-101 or a pharmaceutically acceptable salt thereof.

6. The method of claim 5 wherein the malaria is resistant.

7. The method of claim 5 wherein the composition comprises CEM-101.

8. The method of claim 1 wherein the composition comprises CEM-101.

9. The method of claim 8 wherein the infection is a *Mycobacterium avium* complex infection.

10. The method of claim 8 wherein the infection is a *Mycobacterium tuberculosis* infection.

11. The method of claim 8 wherein the infection is a *Nocardia* infection.

12. The method of claim 8 wherein the infection is a *Plasmodium falciparum* or *Plasmodium berghei* infection.

13. A method for treating a disease selected from the group consisting of tuberculosis, leprosy, and nocardiosis, the method comprising the step of administering to the patient a therapeutically effective amount of a composition comprising CEM-101 or a pharmaceutically acceptable salt thereof.

14. The method of claim 13 wherein the composition comprises CEM-101.

15. The method of claim 14 wherein the disease is tuberculosis.

16. The method of claim 14 wherein the disease is leprosy.

17. The method of claim 14 wherein the disease is nocardiosis.

\* \* \* \* \*